United States Patent [19]

den Otter

[11] 4,359,409
[45] Nov. 16, 1982

[54] CATALYST PREPARATION

[75] Inventor: Gerrit J. den Otter, Amsterdam, Netherlands

[73] Assignee: Shell Oil Company, Houston, Tex.

[21] Appl. No.: 277,359

[22] Filed: Jun. 25, 1981

[30] Foreign Application Priority Data

Aug. 26, 1980 [NL] Netherlands ..................... 8004797

[51] Int. Cl.$^3$ .............................................. B01J 29/22
[52] U.S. Cl. .................................................. 252/455 Z
[58] Field of Search ...................... 252/455 Z; 208/138

[56] References Cited

U.S. PATENT DOCUMENTS

| | | | |
|---|---|---|---|
| 3,376,215 | 4/1968 | Bertolacini et al. | 252/455 Z |
| 3,511,773 | 5/1970 | Addison et al. | 208/138 X |
| 3,691,009 | 9/1972 | Young | 423/328 X |
| 3,953,320 | 4/1976 | Peck et al. | 252/455 Z |
| 4,018,711 | 4/1977 | Bertolacini | 252/455 Z |
| 4,151,121 | 4/1979 | Gladrow | 252/455 Z |

Primary Examiner—Carl F. Dees
Attorney, Agent, or Firm—Dean F. Vance

[57] ABSTRACT

Catalysts for the isomerization of n-paraffins are prepared by treating mordenite with an acid solution comprising Na- or K-ions and thereafter with a solution of an $NH_4$-compound, mixing the thus treated mordenite with an inert binder material on which a Group VIII noble metal has been deposited and finally shaping the resulting mixture under high pressure.

9 Claims, No Drawings

CATALYST PREPARATION

BACKGROUND OF THE INVENTION

1. Field of the Invention

The invention relates to a process for the preparation of a catalyst suitable for use in the isomerization of normal paraffins.

2. Description of the Prior Art

Catalysts that have been prepared by depositing one or more noble metals of group VIII on mordenite have a high activity and selectivity for the isomerization of normal paraffins. For the catalysts to be suitable for this purpose the exchangeable metal cations originally present in the mordenite should be replaced almost completely by hydrogen ions. This replacement may be carried out by treating the mordenite with an aqueous solution of an acid or by treating the mordenite with an aqueous solution of an ammonium compound and subsequently calcining it. See, e.g., U.S. Pat. No. 3,301,917.

As taught in U.S. Pat. No. 3,442,794, catalysts prepared by depositing one or more noble metals of group VIII on mordenite, which mordenite had previously been treated with an aqueous solution of an acid and subsequently with an aqueous solution of an ammonium compound, have a greater activity in the isomerization of normal paraffins than catalysts prepared by depositing one or more noble metals of group VIII on mordenite, which mordenite had been treated either with an aqueous solution of an acid or with an aqueous solution of an ammonium compound. Futher, as taught in U.S. Pat. No. 3,691,009 and U.K. Patent application No. 277/74 filed Jan. 3, 1974, in the isomerization of normal paraffins the activity of the catalysts prepared by depositing one or more noble metals of group VIII on mordenite that had been subjected to the abovementioned two-step treatment, could still be improved considerably by carrying out the acid treatment of the mordenite with a solution prepared by incorporating potassium and/or sodium ions in an aqueous acid solution with a normality of at least 0.5 and at most 3.0, in an amount which, expressed in grams per liter (g/l), is at least ten times the normality of the aqueous acid solution.

From the catalyst base material obtained in the way described above, catalyst particles can be prepared by shaping under high pressure. In order to give these catalyst particles sufficient crushing strength for use on a technical scale, it is common practice to mix the catalyst base material thoroughly with an amorphous binder material consisting substantially of one or more oxides of metals of the groups II, III and IV, before subjecting it to shaping under high pressure.

It had been found in the past that the improved activity for the isomerization of normal paraffins, which improvement had been obtained by replacing the classic one-step treatment of the mordenite by the two-step treatment, using an aqueous acid solution in which no alkali metal ions had been incorporated, is fully retained when the catalyst base material is thoroughly mixed with an amorphous binder material, before shaping under high pressure. Therefore, it was assumed that this retention of activity would apply also to the additional improvement obtained by incorporating alkali metal ions in the aqueous acid solution. This assumption was found to be incorrect. It was found experimentally that, if the mordenite present in the catalyst base material had been subjected to the two-step treatment, using an aqueous acid solution in which alkali metal ions had been incorporated, the additional improvement obtained by incorporating alkali metal ions in the aqueous acid solution was completely lost when the catalyst base material was mixed with an amorphous binder material, before shaping under high pressure. What is needed is some process change wherein the improved activity of the alkali metal-modified catalyst is retained after mixing with an amorphous binder material.

SUMMARY OF THE INVENTION

The present invention encompasses a process to prepare catalyst particles with sufficient crushing strength for use on a technical scale, while retaining the earlier established optimum suitability for the isomerization of normal paraffins, which suitability is obtained by subjecting the mordenite to the two-step treatment, using an aqueous solution of an acid in which alkali metal ions have been incorporated. It was found that such catalyst particles can be prepared by depositing the noble metals of group VIII, not, as usual, on the treated mordenite, but rather on the amorphous binder material. By thoroughly mixing the treated mordenite and the amorphous binder material loaded with the noble metal of group VIII and shaping the mixture thus obtained under high pressure, catalysts can be prepared which actually satisfy the two above-mentioned requirements.

In a specific embodiment, the present invention relates to a process for the preparation of a catalyst suitable for the isomerization of normal paraffins, which process comprises:

(a) treating mordenite with a solution prepared by incorporating potassium and/or sodium ions in an aqueous acid solution having a normality between 0.5 and 3.0, in an amount which, expressed in grams per liter, is at least ten times the normality of the aqueous acid solution;

(b) treating the resulting mordenite with an aqueous solution of an ammonium compound, therein forming ammonium mordenite;

(c) mixing said ammonium mordenite with an amorphous material consisting essentially of one or more oxides of metals of groups II, III and IV, on which amorphous material one or more noble metals of group VIII have been deposited; and (d) subjecting the resulting mixture to shaping under high pressure.

DETAILED DESCRIPTION OF THE INVENTION

For the acid treatment according to the invention both organic and inorganic acids may be used. Preference is given to an aqueous solution of hydrochloric acid. The preferred normality of the aqueous acid solution is between 1.0 and 2.0. For the incorporation of potassium and/or sodium ions in the aqueous acid solution both organic and inorganic salts may be used. Very attractive results can be obtained by carrying out the acid treatment with an aqueous solution of one or more acids, which solution is saturated with one or more potassium and/or sodium salts. For the acid treatment preference is given to an aqueous acid solution containing sodium ions. It is further preferred to make use of potassium and/or sodium salts derived from the same acid as used for the acid treatment. The acid treatment is preferably carried out at elevated temperature, in particular near the boiling point of the aqueous acid solution.

For the treatment of the mordenite with an aqueous solution of an ammonium compound both organic and inorganic ammonium compounds may be used. The term "ammonium compound" is meant to denote any compound able to form ammonium ions. It is preferred to use simple inorganic ammonium compounds, in particular, ammonium nitrate. The preferred molarity of the aqueous solution of the ammonium compound is 0.1 to 10. The treatment with the aqueous solution of an ammonium compound may be carried out at room temperature or at elevated temperature.

The time required for each of the treatments depends on concentration, temperature and degree of contact. As a rule, each treatment should continue for at least 30 minutes and preferably for about one hour. It may be advantageous to repeat the acid treatment or the treatment with an ammonium compound, or even both treatments, several times. It is preferred to repeat or continue the treatment with the aqueous solution of an ammonium compound until the mordenite does not give off any more alkali metal in amounts detectable by analysis.

After the treatment with an ammonium compound the mordenite is in the ammonium form. By calcining the ammonium mordenite, nitrogen atoms incorporated by the treatment are removed and mordenite in the hydrogen form is obtained. The conversion of the ammonium mordenite into the hydrogen form may take place both before and after mixing with the amorphous material loaded with the noble metal of group VIII.

In the catalyst preparation according to the invention, the treated mordenite is mixed with an amorphous material consisting substantially of one or more oxides of elements of the groups II, III and IV, on which amorphous material one or more noble metals of group VIII have been deposited. Examples of amorphous materials suitable for use as carriers for the noble metals of group VIII are alumina, silica, magnesia, zirconia and boria. Preference is given to alumina. The noble metals of group VIII which may be present on the amorphous material are platinum, palladium, rhodium, ruthenium, iridium and osmium, of which platinum is the preferred metal. The catalyst may contain two or more noble metals of group VIII. The amount of noble metal of group VIII present in the ready catalyst is preferably 0.01 to 5% weight (w) and in particular 0.1 to 1.5% w. The term "ready catalyst" refers to the mixture of treated mordenite and treated amorphous material. The ready catalyst contains preferably 5 to 50% w amorphous material loaded with noble metal of group VIII. The noble metals of group VIII are preferably deposited on the amorphous carrier materials by impregnation. The shaping at high pressure may be carried out, for instance by tabletting or extrusion.

Catalysts according to the invention are very suitable for the isomerization of normal paraffins in the presence of hydrogen. The normal paraffins which are subjected to the isomerization treatment contain preferably 4 to 10 and in particular 4 to 7 carbon atoms per modecule. The isomerization of the above-mentioned low-molecular normal paraffins in the presence of hydrogen is usually carried out at a temperature of 150° to 300° C., at a pressure of 3 to 50 bar, a space velocity, based on H-mordenite, of 0.5 to 10 $kg.kg^{-1}.h^{-1}$ and a molar ratio of hydrogen to feed of 0.5:1 to 10:1. The isomerization is preferably carried out under the following conditions: a temperature of 230° to 280° C., a pressure of 10 to 40 bar and a space velocity based on H-mordenite, of 1.0 to 5.0 $kg. kg^{-1}.h^{-1}$.

The isomerization of low-molecular normal paraffins is an attractive method for the upgrading of light gasoline fractions, such as tops obtained by straight-run distillation. In comparison with isoparaffins with the same number of carbon atoms, normal paraffins have a low octane number. Therefore, their presence in light gasoline fractions is undesirable. By conversion of the normal paraffins present in the fractions into isoparaffins, the octane number is increased. Isoparaffins also present in these gasoline fractions may be removed from them before the isomerization, for instance by distillation or by means of molecular sieves. Since isomerization of normal paraffins is an equilibrium reaction, the product leaving the isomerization reactor still contains an amount of unconverted normal paraffins. These paraffins may be separated for the isomerization product, for instance by distillation or by means of molecular sieves, and recycled to the isomerization process. It is also possible to add the isomerization product to the original mixture of normal and isoparaffins, to remove the isoparaffins from this mixture, for instance by distillation or with molecular sieves, and to isomerize the remaining mixture of normal paraffins according to the invention.

The invention will now be explained with reference to the following example, which is given for the purpose of illustration only and is not meant to limit the invention to the particular reactants and conditions employed.

EXAMPLE

In the example five catalysts were involved, which had been prepared as follows:

Catalyst 1

A mixture of 20 grams (g) sodium mordenite and 200 milliliters (ml) 1.5 N HCl was boiled under reflux for one hour. The solid material was filtered off and washed with water. Subsequently, the solid material was boiled under reflux for one hour with 200 ml of a 1.0 molar $NH_4NO_3$ solution. This treatment with $NH_4NO_3$ was repeated twice, each time with a fresh $NH_4NO_3$ solution. After each treatment the solid material was filtered off and washed with water. Eventually platinum was deposited on the $NH_4$ mordenite thus obtained by treating it with an aqueous solution of a platinum compound. The solid material was filtered off and dried at 120° C. The $Pt/NH_4$ mordenite thus obtained was tabletted at a pressure of 50 tons and ground. From the ground material a fraction with particle diameters between 0.2 and 0.6 mm was separated by sieving. This sieve fraction was converted into catalyst 1 by calcining at 500° C.

Catalyst 2

The catalyst was prepared in substantially the same way as catalyst 1, the difference being that in the present case the $Pt/NH_4$ mordenite was thoroughly mixed with a powdered alumina in a weight ratio of 4:1, before being pelletized.

Catalyst 3

This catalyst was prepared in substantially the same way as catalyst 1, the difference being that in this case use was made of 1.5 N HCl to which 400 g NaCl/l had been added.

Catalyst 4

This catalyst was prepared in substantially the same way as catalyst 3, the difference being that in the present case the Pt/NH$_4$ mordenite was thoroughly mixed, in a weight ratio of 4:1, with the same alumina powder as used in the preparation of catalyst 2, before being tabletted.

Catalyst 5

A Pt/alumina composite containing 1.2 parts by weight (pbw) platinum per 100 pbw alumina was prepared by treating the alumina powder which was also used in the preparation of the catalysts 2 and 4 with an aqueous solution of a platinum compound, followed by drying and calcining at 500° C. NH$_4$ mordenite, obtained as intermediate product in the preparation of the catalysts 3 and 4, was dried at 120° C. and thoroughly mixed in a weight ratio of 4:1 with the above-mentioned Pt/alumina composite. The mixture was tabletted at a pressure of 50 tons and ground. From the ground material a fraction with particle diameters between 0.2 and 0.6 mm was separated by sieving. This sieve fraction was converted into catalyst 5 by calcining at 500° C.

Isomerization Experiments

The above-mentioned five catalysts, all containing 0.3 pbw platinum, based on 100 pbw H-mordenite, were used for the isomerization of n-pentane. The isomerization was carried out under the following conditions:

| | |
|---|---|
| Temperature | 250° C. |
| Pressure | 30 bar |
| Space velocity, based on H—mordenite | 2 kg.kg$^{-1}$.h$^{-1}$. |
| Molar ratio H$_2$/feed | 1.25 |
| Duration of the experiment | 25 hours |

The results of these experiments are listed in the table. The percentages by weight of isopentane in the product are the averages between the run hours 10 and 25.

TABLE

| Experiment Number | Catalyst Number | % w isopentane in product |
|---|---|---|
| 1 | 1 | 64.1 |
| 2 | 2 | 64.0 |
| 3 | 3 | 67.3 |
| 4 | 4 | 63.5 |
| 5 | 5 | 66.9 |

Of the experiments 1–5, only experiment 5 is an isomerization experiment according to the present invention. In experiment 5 a catalyst was used which had been prepared according to the invention. The other experiments are outside the scope of the invention and have been included for comparison.

Comparison of the results of the experiments 1 and 2 shows that mixing of the Pt/H mordenite with the Al$_2$O$_3$ binder before shaping under high pressure has no influence in the activity of the ready catalyst particles.

Comparison of the results of the experiments 3 and 4 shows that the improvement in the activity of the H-mordenite as a result of the incorporation of sodium ions in the acid solution is completely lost when the Pt/H mordenite is mixed with the Al$_2$O$_3$ binder prior to shaping under high pressure. It should be noted that catalyst number 3 is not acceptable for commercial application in view of its low crush strength.

The result of experiment 5 shows that in the preparation of the catalyst particles according to the present invention the improvement in the activity of the H-mordenite as a result of incorporating sodium ions in the acid solution is fully retained in the ready catalyst particles. The catalyst of experiment 5 not only retains an excellent activity, but also has sufficient crush strength for commercial applications.

What is claimed is:

1. A process for the preparation of a catalyst suitable for the isomerization of normal paraffins, which process comprises;
   (a) treating mordenite with a solution prepared by incorporating potassium and/or sodium ions in an aqueous acid solution having a normality between 0.5 and 3.0, in an amount which, expressed in grams per liter, is at least ten times the normality of the aqueous acid solution;
   (b) treating the resulting mordenite with an aqueous solution of an ammonium compound, therein forming ammonium mordenite;
   (c) mixing said ammonium mordenite with an amorphous material consisting essentially of one or more oxides of metals of groups II, III and IV, on which amorphous material one or more noble metals of group VIII have been deposited; and
   (d) subjecting the resulting mixture to shaping under high pressure.

2. The process according to claim 1, wherein the acid treatment of step a is carried out at elevated temperature, using an aqueous hydrochloric acid solution with a normality between 1.0 and 2.0, which solution has been saturated with sodium chloride.

3. The process according to claim 1 or 2, wherein the treatment with the ammonium compound in step b is carried out with an aqueous solution of ammonium nitrate having a molarity of 0.1 to 10.

4. The process according to claim 1 wherein the treatment with the ammonium compound in step b is repeated until the mordenite does not give off any more alkali metal in amounts detectable by analysis.

5. The process according to claim 1 wherein said amorphous material is alumina.

6. The process according to claim 1, wherein said noble metal is platinum.

7. The process according to claim 1, wherein said resulting mixture of step d contains 0.1 to 1.5% weight noble metal of group VIII.

8. The process according to claim 1, wherein the resulting mixture of step d contains 5–50 percent by weight amorphous material loaded with noble metal of group VIII.

9. A catalyst suitable for the isomerization of normal paraffins, prepared according to the process of claim 1.

* * * * *